(12) United States Patent
Rainer et al.

(10) Patent No.: US 8,528,399 B2
(45) Date of Patent: Sep. 10, 2013

(54) METHODS AND APPARATUSES FOR MEASURING PROPERTIES OF A SUBSTANCE IN A PROCESS STREAM

(75) Inventors: Michael D. Rainer, Burton, OH (US); Peter J. Gillespie, Chagrin Falls, OH (US); Douglas J. Paige, Lakewood, OH (US); Kenneth J. Maynard, Amherst, OH (US)

(73) Assignee: The Mercury Iron and Steel Co., Cleveland, OH (US)

( * ) Notice: Subject to any disclaimer, the term of this patent is extended or adjusted under 35 U.S.C. 154(b) by 352 days.

(21) Appl. No.: 13/107,675

(22) Filed: May 13, 2011

(65) Prior Publication Data

US 2012/0118058 A1 May 17, 2012

Related U.S. Application Data

(60) Provisional application No. 61/347,098, filed on May 21, 2010.

(51) Int. Cl.
*G01F 1/68* (2006.01)
*G01N 21/41* (2006.01)

(52) U.S. Cl.
USPC .................................. 73/204.11; 356/135

(58) Field of Classification Search
USPC ............... 73/204.11; 356/128–137, 335–343
See application file for complete search history.

(56) References Cited

U.S. PATENT DOCUMENTS

| | | | |
|---|---|---|---|
| 4,182,362 A | 1/1980 | Hewson et al. | |
| 4,726,399 A | 2/1988 | Miller | |
| 5,342,126 A | 8/1994 | Heston et al. | |
| 5,583,300 A | 12/1996 | Green et al. | |
| 5,988,203 A | 11/1999 | Hutton | |
| 6,000,290 A | 12/1999 | Benton et al. | |
| 6,000,427 A | 12/1999 | Hutton | |
| 6,067,151 A | 5/2000 | Salo | |
| 6,170,515 B1 | 1/2001 | Peterson et al. | |
| 6,196,256 B1 | 3/2001 | Klampfer | |
| 6,374,859 B1 | 4/2002 | Vu et al. | |
| 6,675,658 B2 | 1/2004 | Petrich et al. | |
| 6,760,098 B2 | 7/2004 | Salo | |
| 6,886,606 B2 | 5/2005 | Few et al. | |
| 6,892,762 B2 | 5/2005 | Porter et al. | |
| 7,172,572 B2 | 2/2007 | Diamond et al. | |
| D562,169 S | 2/2008 | Oshima et al. | |
| 7,343,933 B2 | 3/2008 | McBeth et al. | |
| D587,611 S | 3/2009 | Oshima et al. | |

(Continued)

FOREIGN PATENT DOCUMENTS

DE 19855218 A1 8/1999

OTHER PUBLICATIONS

Pending Design U.S. Appl. No. 29/408,355, Sensing Apparatus, Michael D. Rainer et al., filed Dec. 12, 2011.

(Continued)

*Primary Examiner* — Harshad R Patel
*Assistant Examiner* — Brandi N Hopkins
(74) *Attorney, Agent, or Firm* — Ulmer & Berne LLP

(57) ABSTRACT

A flow-through sensing apparatus includes a flow-head and a sensor that are configured to be selectively coupled through use of a quick-disconnect mechanical coupling. When the sensor is coupled with the flow-head, the sensor cooperates with the flow-head to at least partially define a sensing chamber. The sensor is configured to determine a process parameter, such as refractive index, regarding a substance in the sensing chamber.

24 Claims, 9 Drawing Sheets

(56) References Cited

U.S. PATENT DOCUMENTS

| | | | |
|---|---|---|---|
| 7,509,855 | B2 | 3/2009 | Garvin |
| D602,794 | S | 10/2009 | Oshima |
| D609,591 | S | 2/2010 | Oshima et al. |
| 2008/0006085 | A1 | 1/2008 | Yamashita et al. |
| 2008/0135116 | A1 | 6/2008 | Sugiura et al. |
| 2009/0025472 | A1 | 1/2009 | Garvin |
| 2010/0064799 | A1 | 3/2010 | Mais et al. |

OTHER PUBLICATIONS

Bronkhorst High-Tech, document entitled, "Flow-SMS: Mass Flow Surface Mount Solutions", Apr. 2006, 1 page. Depicted components believed to be in public use prior to May 21, 2009.

Bronkhorst High-Tech, document entitled, "Mani-Flow: Customised Manifold Solutions for Mass Flow and Pressure", Jul. 2006, 1 page. Depicted components believed to be in public use prior to May 21, 2009.

Burkert Fluid Control Systems, document entitled, "INLINE fitting with paddle-wheel for flow measurement", Jul. 5, 2010, 10 pages. Depicted components believed to be in public use prior to May 21, 2009.

Burkert Fluid Control Systems, document entitled, "Positive displacement flow fitting for continuous measurement and batch control", Sep. 21, 2010, 4 pages. Depicted components believed to be in public use prior to May 21, 2009.

Innovative Waters, LLC, document entitled, "Manifolds", www.innovativewaters.com/manifold.html, 2009, retrieved Oct. 19, 2010, 2 pages. Depicted components believed to be in public use prior to May 21, 2009.

Omega Engineering, Inc., document entitled, "Industrial pH Instrumentation & Electronics Retractable Lock-N-Load ALpHA pH/ORP Electrode Assemblies", Sep. 2009, 3 pages. Depicted components believed to be in public use prior to May 21, 2009.

Jetalon Solutions, Inc., document entitled, "Concentration Monitor NX-148 Hammerhead", Jun. 2010, 2 pages. Depicted components believed to be in public use prior to May 21, 2009.

Swagelok Company, manual entitled, "Swagelok CR-288 Concentration Monitor User's Manual", Jun. 2006, 32 pages. Depicted components believed to be in public use prior to May 21, 2009.

K-Patents, Inc., manual entitled, "Semicon Process Refractometer PR-33-S", Mar. 2010, 38 pages. Depicted components believed to be in public use prior to May 21, 2009.

K-Patents, Inc., document entitled, "Concentration Monitoring of Fab Chemicals In Cleanroom Environments", Jan. 2009, 6 pages. Depicted components believed to be in public use prior to May 21, 2009.

K-Patents, Inc., document entitled, "PR-33-S Sensor Installation", 2 pages. Depicted components believed to be in public use prior to May 21, 2009.

Mettler Toledo, manual entitled, "InFlow 751 Instruction Manual", Sep. 1997, 7 pages. Depicted components believed to be in public use prior to May 21, 2009.

Omega Engineering, Inc., document entitled, "Industrial pH Instrumentation & Electrodes Flat Surface pH/ORP Industrial Electrodes", Mar. 2009, 3 pages. Depicted components believed to be in public use prior to May 21, 2009.

Omega Engineering, Inc., document entitled, "Industrial pH Instrumentation & Electrodes In Line Flat Surface pH/ORP Electrodes", Mar. 2009, 2 pages. Depicted components believed to be in public use prior to May 21, 2009.

HM Digital, Inc., document entitled, "SM-1: In-Line Single TDS Monitor", www.tdsmeter.com/products/sm1.html, retrieved Oct. 19, 2010, 1 page. Depicted components believed to be in public use prior to May 21, 2009.

"The PR-1000 Inline Process Refractometer", AFAB Enterprises, May 5, 2009, 25 pages. Depicted components believed to be in public use prior to May 21, 2009.

Pending Design U.S. Appl. No. 29/365,064, Sensing Apparatus, Michael D. Rainer et al., filed Jul. 2, 2010.

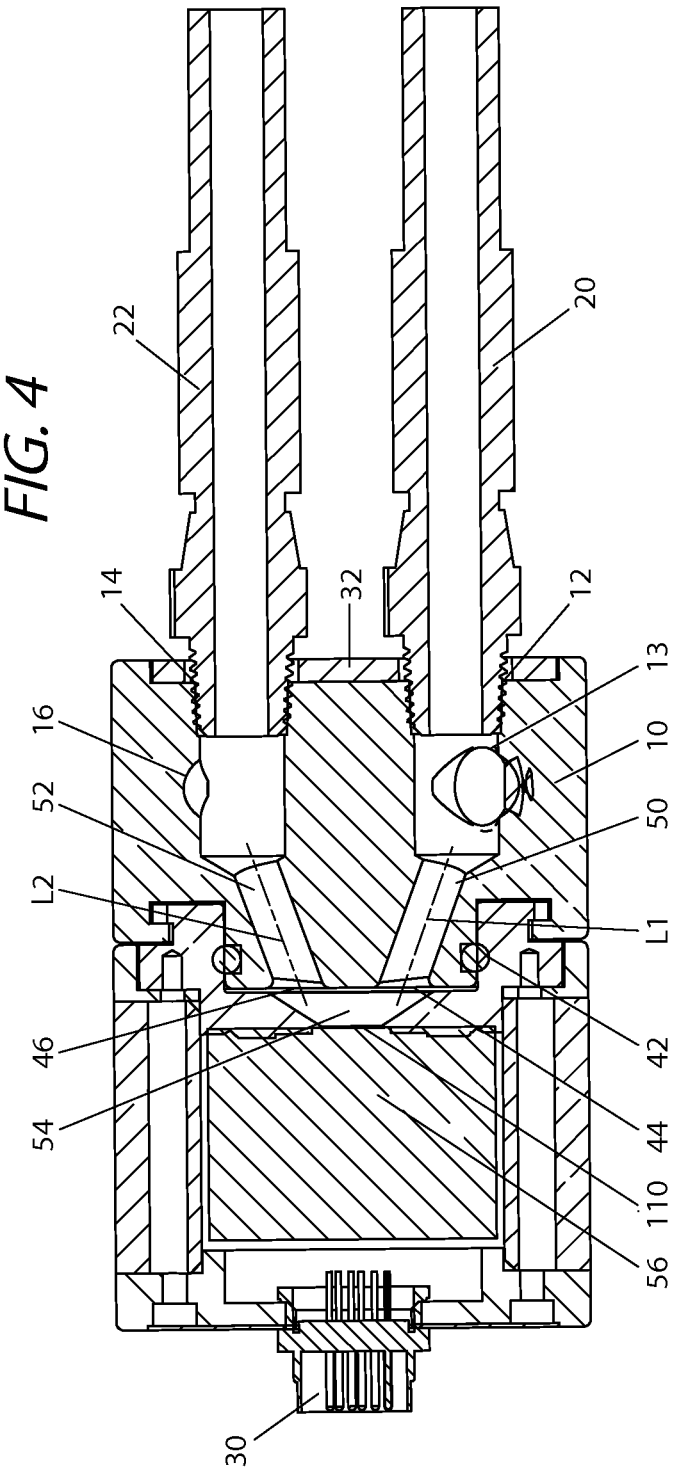

METHODS AND APPARATUSES FOR MEASURING PROPERTIES OF A SUBSTANCE IN A PROCESS STREAM

REFERENCE TO RELATED APPLICATION

The present application claims priority of U.S. provisional application Ser. No. 61/347,098 filed May 21, 2010, and hereby incorporates the same provisional application herein by reference in its entirety.

TECHNICAL FIELD

A flow-through sensing apparatus is provided and is configured for sensing one or more physical properties or process parameters regarding a substance of interest.

BACKGROUND

Conventional in-line sensors monitor physical properties or process parameters regarding fluid flowing through pipes or other conduits. In many instances, installation, calibration or replacement of conventional in-line sensors requires temporarily stopping the flow of fluid through the conduits, or disconnecting the conduits.

SUMMARY

In accordance with one embodiment, a flow-through sensing apparatus comprises a flow-head and a sensor. The flow-head defines an input port and an output port and comprises a first mating feature. The sensor comprises a sensing element and a second mating feature. The first mating feature is configured to selectively engage the second mating feature in a twist-lock configuration to provide a quick-disconnect mechanical coupling between the sensor and the flow-head. When the sensor is coupled with the flow-head, the sensor cooperates with the flow-head to at least partially define a sensing chamber. The sensing chamber is in fluid communication with each of the input port, the output port, and the sensing element. The sensing element is configured to determine the refractive index of a substance in the sensing chamber.

In accordance with another embodiment, a flow-through sensing apparatus comprises a flow-head and a sensor. The flow-head defines an input port and an output port. The sensor comprises a sensing element. The flow-head and the sensor cooperate to define means for quick-disconnect mechanically coupling the sensor and the flow-head. When the sensor is coupled with the flow-head, the sensor cooperates with the flow-head to at least partially define a sensing chamber. The sensing chamber is in fluid communication with each of the input port, the output port, and the sensing element.

In accordance with yet another embodiment, a sensor is configured for quick-disconnect mechanical coupling with a flow-head. The sensor comprises a sensing element and a mating feature. The mating feature is configured to selectively engage a flow-head in a twist-lock configuration to provide a quick-disconnect mechanical coupling between the sensor and a flow-head. When the sensor is coupled with a flow-head, the sensor cooperates to at least partially define a sensing chamber. The sensing chamber is in fluid communication with the sensing element. The sensing element is configured to determine the refractive index of substance in the sensing chamber.

BRIEF DESCRIPTION OF THE DRAWINGS

It is believed that certain embodiments will be better understood from the following description taken in conjunction with the accompanying drawings in which:

FIG. 4 is a cross-sectional view depicting the components of FIG. 1;

DETAILED DESCRIPTION

Figure 1:
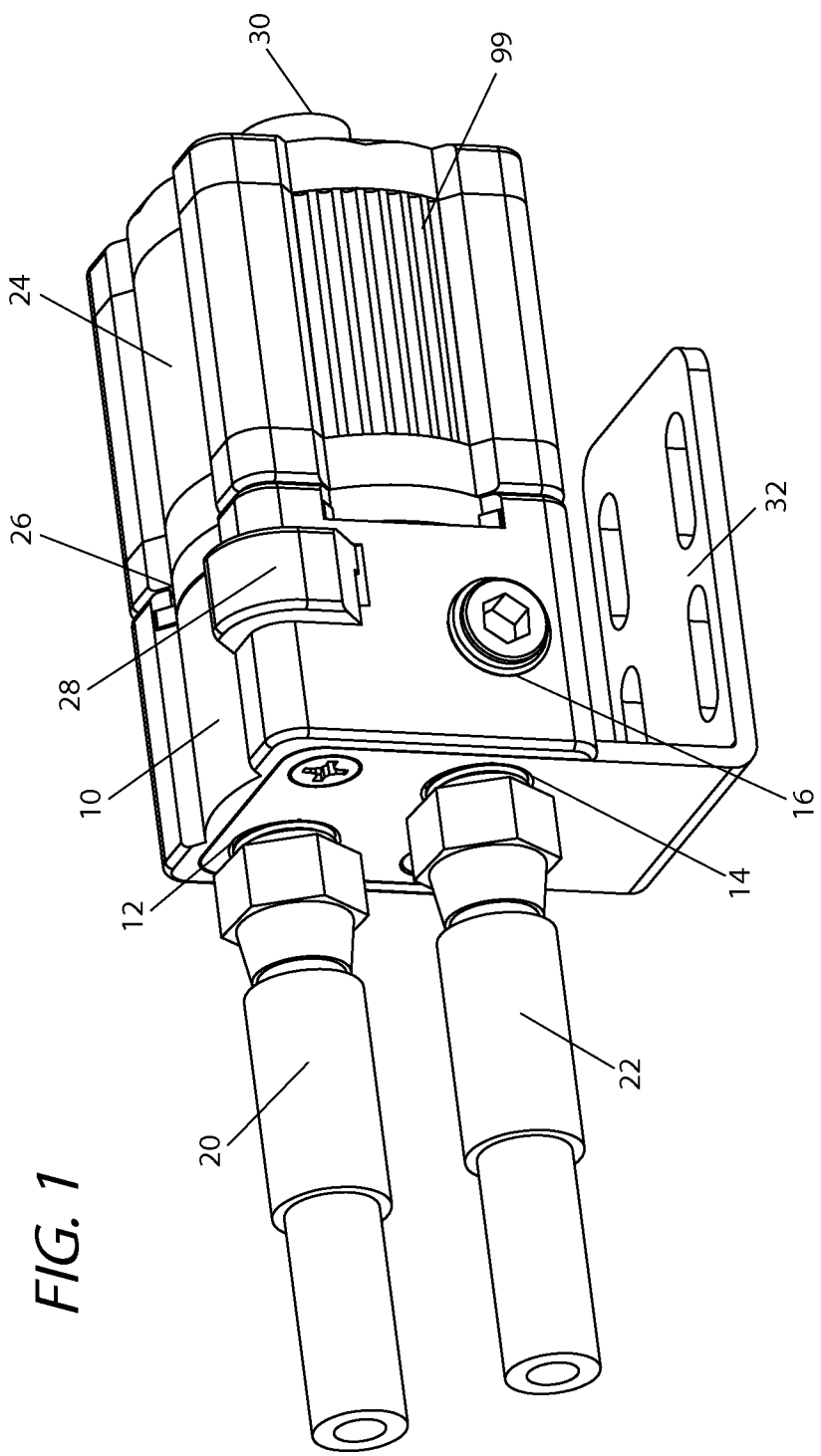
FIG. 1 is a front perspective view depicting a flow-through sensing apparatus in accordance with one embodiment, wherein the flow-through sensing apparatus is in association with a portion of a supply conduit and a portion of a discharge conduit.

FIG. 1 illustrates a flow-through sensing apparatus in its assembled state. According to this embodiment, the flow-through sensing apparatus comprises an integrated flow-head 10 having multiple ports 12, 13, 14, and 16, a sensor 24 that is removably connected to flow-head 10 by way of a quick-disconnect coupling 26, a retractable locking mechanism 28 for locking sensor 24 to flow-head 10, a communication element 30 for receiving power and/or communicating with external devices, and a mounting bracket 32 which can be used to mount the apparatus to another object. At least one of the ports 12, 13, 14, and 16 can be configured as an input port, while at least one other one of the ports 12, 13, 14, and 16 can be configured as an output port. In one embodiment, at least one of the ports 12, 13, 14, and 16 can comprise a respective threaded aperture in the flow-head 10. However, it will be appreciated that one or more of the ports 12, 13, 14, and 16 might not be threaded. For example, with reference to the flow-through sensing apparatus of FIGS. 9A-9D, a flow-head can include only two ports (i.e., a single input port and a single output port), and each of those ports can comprise a respective push-type compression fitting such as for receiving plastic or metal tubing as generally shown. In still other embodiments, ports on a flow-head can comprise hose barb type fittings, tubing, or any of a variety of other suitable types of fittings or connections.

The flow-through sensing apparatus can be positioned in a bypass stream that runs in parallel to a main process stream containing a substance of interest. A substance from the main process stream can be diverted to the flow-through sensing apparatus by a supply conduit 20 and likewise, be carried away from the apparatus by a discharge conduit 22.

Supply conduit 20 and discharge conduit 22 can each comprise any of a variety of suitable rigid or flexible hose, tubing, piping or other plumbing conveyance for conveying or conducting a test substance to and from the apparatus. Examples include readily available off-the-shelf tube fittings, hose couplings, pipe fittings, quick-disconnect fittings, instrumentation fittings, compression fittings, and the like.

The substance of interest can be a fluid which includes, but is not limited to, any single one or combination of liquids, gasses, or solids, including homogenous or non-homogeneous mixtures, emulsions, or colloidal solutions. The force required to cause the substance to flow through the flow-through sensing apparatus can be generated by any of a variety of sources including, for example, gravity feed, external pumps, pressure or temperature differential, chemical reaction, or the like. Alternatively, this force can be generated from an internal pumping assembly located within flow-head 10.

Although the flow-through sensing apparatus is described above as being positioned in a bypass stream, it should be understood that in the embodiments presented herein, nothing limits the flow-through sensing apparatus from being placed in the actual main process stream, should supply conduit 20 and discharge conduit 22 of that process stream be constructed in such a manner as to be compatible with the size and flow-rate parameters of the flow-through sensing apparatus.

Figure 2B:
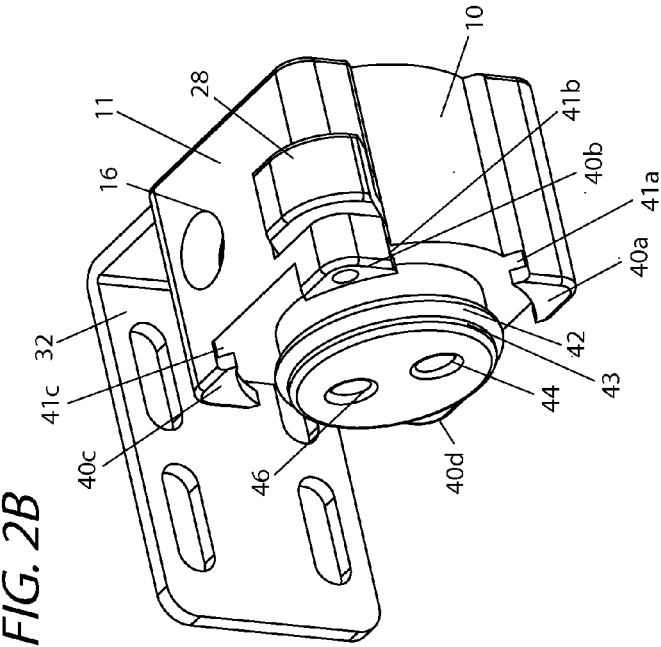
FIG. 2B is a rear perspective view depicting the flow-head of FIG. 2A.

Referring now to FIGS. 2-3, the integrated flow-head 10 is shown to be separated from sensor 24. In this embodiment, the ports 12 and 13 can be configured as input ports for connecting one or more supply conduits (e.g., 20) to selectively convey a substance into flow-head 10, and the ports 14 and 16 can be configured as output ports for connecting one or more discharge conduits (e.g., 22) to selectively convey a substance away from flow-head 10. With reference to FIG. 4, the ports 12 and 13 can each be in fluid communication with an input channel 50 and an input channel opening 44, and ports 14 and 16 can each be in fluid communication with an output channel 52 and an output channel opening 46. When flow-head 10, sensor 24, and a chamber seal 42 are mated in the fully assembled state as shown in FIG. 4, a sensing chamber 54 can be created and provided in communication with both the input channel opening 44 and the output channel opening 46. The chamber seal 42 can be provided on either the sensor 24 or the flow-head 10 and can facilitate a seal between the sensor 24 and the flow-head 10 when the sensor 24 is coupled with the flow-head 10. For example, as shown in FIG. 2B, the flow-head 10 can define an annular channel 43, and the chamber seal 42 can comprise an 0-ring that can be at least partially received within the annular channel 43. It will be appreciated that a chamber seal can be provided in any of a variety of other suitable configurations.

The quick-disconnect coupling 26 can facilitate selective attachment of sensor 24 to flow-head 10, and can facilitate simple and quick removal and replacement of sensor 24 relative to flow-head 10, such as for cleaning and maintenance of sensor 24. More particularly, the quick-disconnect coupling 26 can include one or more mating features on flow-head 10 which can selectively engage one or more corresponding mating features on sensor 24, to join the two components into a single unified fluid-tight assembly. For example, as shown with reference to FIGS. 1, 2A-2B, 3A-3B, and 4, the flow-head 10 can comprise a body 11 and mating features in the form of flanges 40a, 40b, 40c, and 40d extending from the body 11. The sensor 24 can comprise a body 25 and mating features in the form of flanges 48a, 48b, 48c, and 48d extending from the body 25. The flanges 40a, 40b, 40c, and 40d can cooperate with the body 11 to define respective grooves 41a, 41b, 41c, and 41d. The respective mating features of the flow-head 10 and the sensor 24 can selectively engage one another in a twist-lock configuration to provide a quick-disconnect mechanical coupling between the sensor 24 and the flow-head 10. For example, to couple the sensor 24 with the flow-head 10 through the twist-lock action, each of the flanges 48a, 48b, 48c, and 48d can be received within a respective one of the grooves 41a, 41b, 41c, and 41d and sandwiched or compressed between a corresponding respective one of the flanges 40a, 40b, 40c, and 40d and the body 11.

Accordingly, in this configuration, to facilitate the twist-lock action, a partial-turn of the sensor 24 relative to the flow-head 10 can result in movement of the sensor 24 relative to the flow-head 10 between an unlocked position and a fully locked position. FIGS. 1 and 4 illustrate the sensor 24 in the fully locked position relative to the flow-head 10. In the embodiment of FIGS. 1 and 4, an eighth-turn (i.e., 45 degrees) of the sensor 24 relative to the flow-head 10 can achieve movement of the sensor 24 relative to the flow-head 10 between the unlocked position and the fully locked position. However, to facilitate the twist-lock configuration, it will be appreciated that a different amount of rotation less than 360 degrees (e.g., 90 degrees, 120 degrees, or 180 degrees) can alternatively achieve movement of a sensor relative to a flow-head between an unlocked position and a fully locked position. In still other embodiments, a different amount of rotation greater than or equal to 360 degrees can alternatively achieve movement of a sensor relative to a flow-head between an unlocked position and a fully locked position. It will be appreciated that selective mechanical coupling of a flow-head and a sensor can be achieved through use of any of a variety of other suitable mechanical features.

Figure 2C:
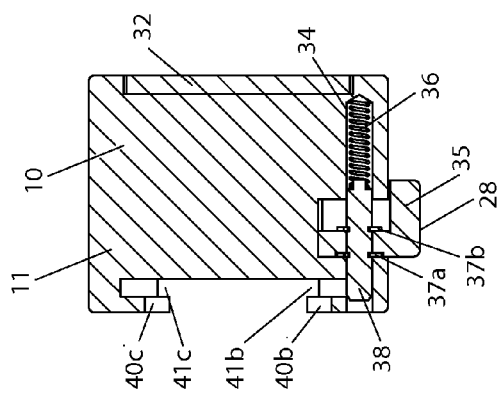
FIG. 2C is a cross-sectional view generally depicting the flow-head of FIG. 2A.
Figure 2A:
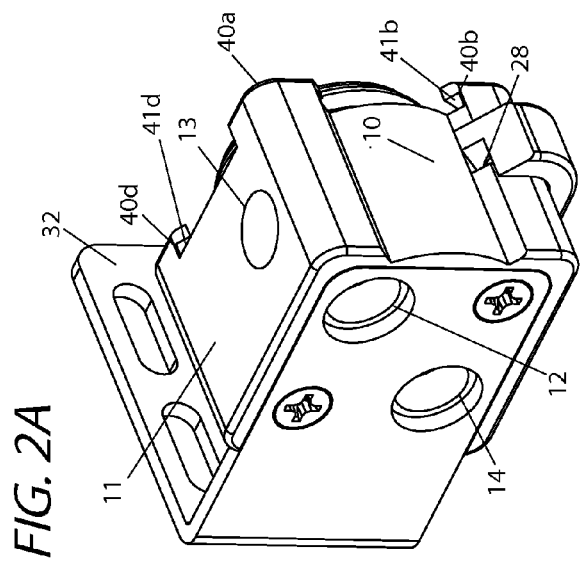
FIG. 2A is a front perspective depicting a flow-head of the flow-through sensing apparatus of FIG. 1, and apart from the remaining components of FIG. 1.
Figure 8:
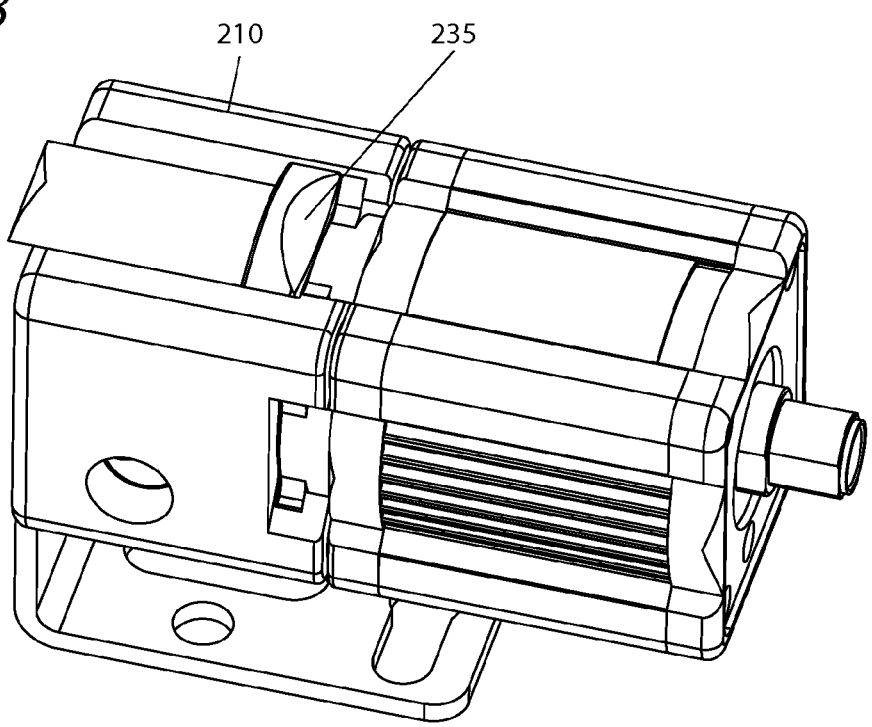
FIG. 8 is a perspective view depicting a flow-through sensing apparatus in accordance with another embodiment.
Figure 9A:
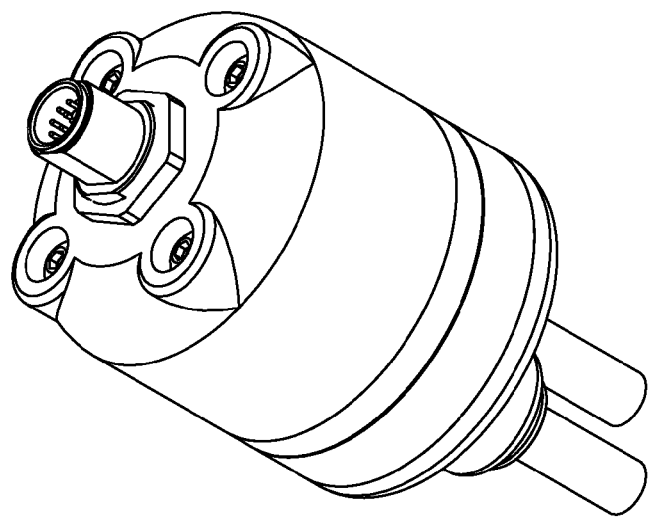
FIG. 9A is a front perspective view depicting a flow-through sensing apparatus in accordance with yet another embodiment, wherein the flow-through sensing apparatus is in association with a portion of a supply conduit and a portion of a discharge conduit.
Figure 9B:
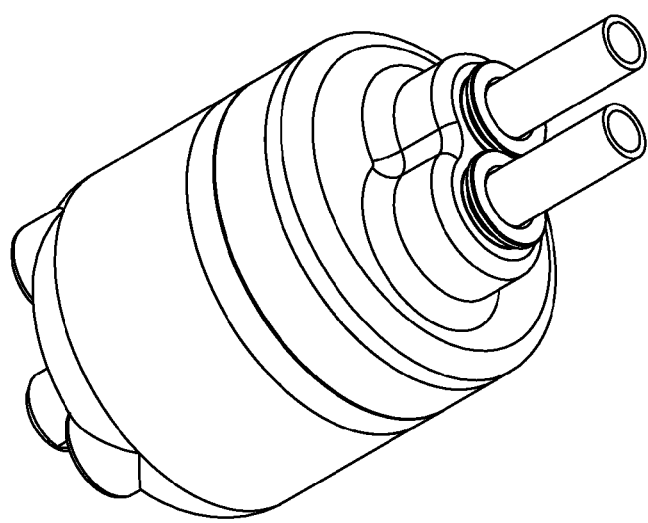
FIG. 9B is a rear perspective view depicting the components of FIG. 9A.
Figure 9C:
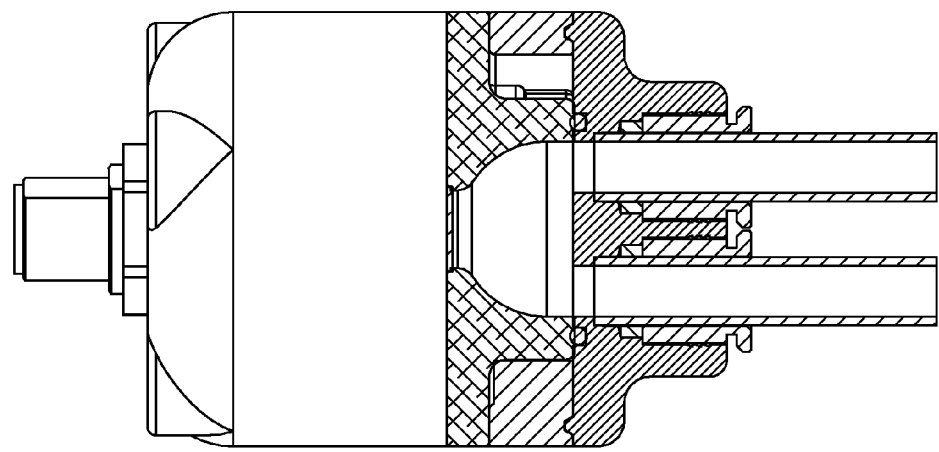
FIG. 9C is a cross-sectional view depicting the components of FIGS. 9A-9B.
Figure 9D:
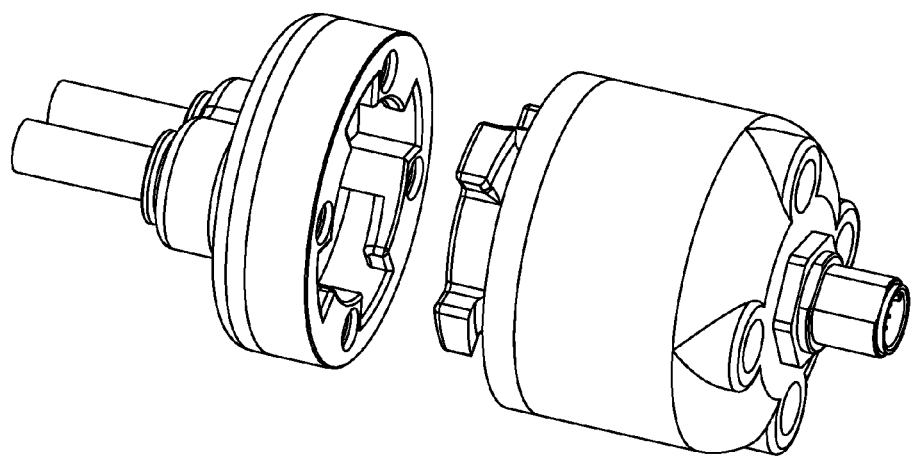
FIG. 9D is a perspective view depicting the components of FIGS. 9A-9C, but wherein the sensor is uncoupled from the flow-head.

When the sensor 24 is in the fully locked position relative to the flow-head 10, the retractable locking mechanism 28 can be selectively operated to prevent inadvertent rotation or unlocking of the sensor 24 relative to the flow-head 10. For example, as shown in FIG. 2C, the flow-head 10 can comprise the retractable locking mechanism 28, which can include a thumb-lever 35 which is attached to a pin 38. A portion of the pin 38 can be slideably received within a bore 34 formed in the flow-head 10, and locking clips 37a and 37b can be provided to position and lock the thumb-lever 35 to the pin 38. An operator can operate the retractable locking mechanism 28 by sliding the thumb-lever 35 along a corner of the flow-head 10. Once the pin 38 is in the retracted position, sensor 24 can be rotated (e.g., 45 degrees) to an unlocked position for removal from the flow-head 10. A spring 36 can be located behind the pin 38 for biasing the thumb-lever 35 to keep the pin 38 engaged when manual pressure on the thumb-lever 35 is absent. It will be appreciated that a retractable locking mechanism can be provided in any of a variety of other configurations. For example, in one alternative configuration, as shown in FIG. 8, a thumb-lever 235 of a retractable locking mechanism can be configured for sliding along an edge face of a flow-head 210. In another alternative embodiment (not shown), a sensor, as opposed to a flow-head (e.g., 10), can comprise a retractable locking mechanism. In lieu of a retractable pin, it will be appreciated that any of a variety of other suitable mechanical devices can be provided to selectively prevent inadvertent rotation or unlocking of the sensor 24 relative to the flow-head 10. It will also be appreciated that a flow-through sensing apparatus might not include any retractable locking mechanism or other locking device such as, for example, with respect to the flow-through sensing apparatus depicted in FIGS. 9A-9D.

The mounting bracket 32 can be attached to a face of flow-head 10 in order to fix flow-head 10 to another object such as a wall, C-channel, or other structure. In the event that sensor 24 were to be removed from flow-head 10, and flow-head 10 were connected to another object by way of mounting bracket 32, then sensor 24 can be removed without the need to disassemble the associated supply conduit 20 and discharge conduit 22 connected to flow-head 10. Although flow-head 10 is shown in FIGS. 1-2 with mounting bracket 32, it should be understood that flow-head 10 can alternatively be independently supported by the plumbing itself, or by other method, and without use or presence of a mounting bracket (e.g., 32).

In one embodiment, flow-head 10 can be equipped with a combination of one or more drain valves, pressure release valves, check valves, and/or over-pressure release valves (not shown). In the event that, after a given number of supply conduits and discharge conduits are connected to flow-head 10, and there remain unconnected input and/or output ports (such as port 16 in FIG. 1), the unused ports can each be manually plugged with an appropriate plug, valve, or shut-off to prevent leakage of the substance (shown with respect to port 16 in FIG. 1).

Figure 3B:
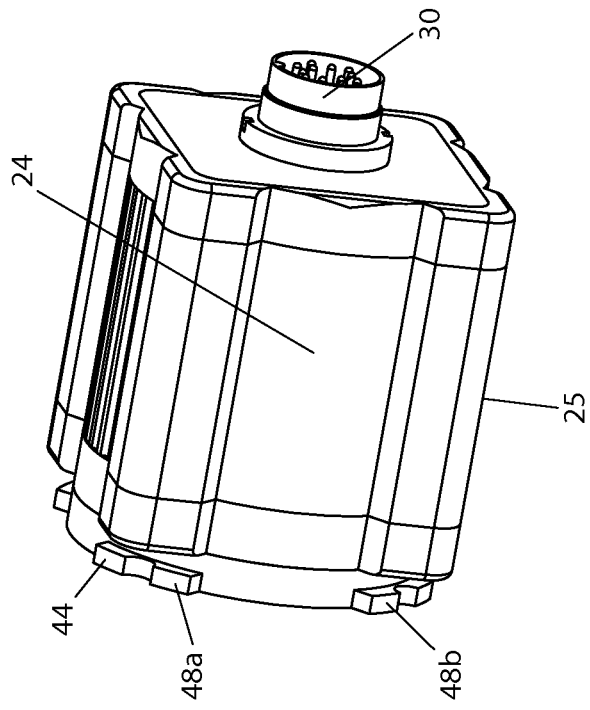
FIG. 3B is a rear perspective view depicting the sensor of FIG. 3A.
Figure 3A:
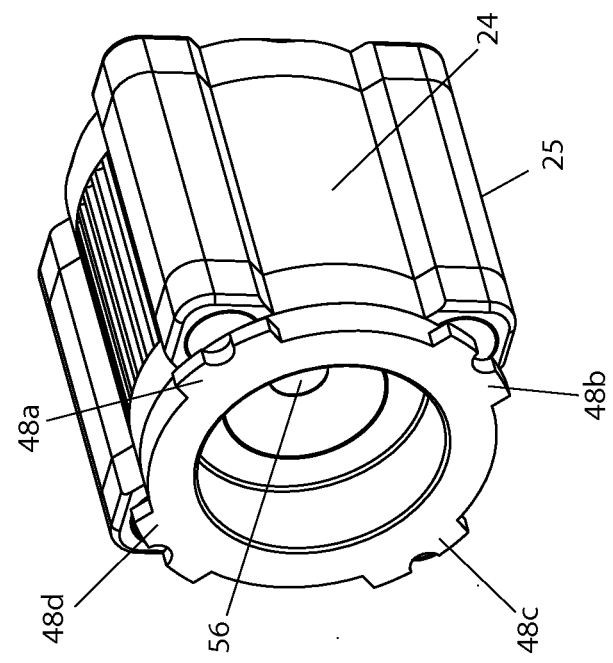
FIG. 3A is a front perspective depicting a sensor of the flow-through sensing apparatus of FIG. 1, and apart from the remaining components of FIG. 1.

The sensor 24 depicted in FIG. 1 is separated from flow-head 10 and is shown in greater detail in FIGS. 3A and 3B. Sensor 24 comprises a sensing element 56 capable of sensing one or more physical properties or process parameters regarding the substance of interest. The sensor 24 can also comprise a microprocessor and/or other electronic circuitry, capable of converting signals from sensing element 56 into usable data or signals to be communicated to external devices. The microprocessor and/or other electronic circuitry can provide sensor 24 with intelligence independent of an external control or processing unit. Sensor 24 can further include a communication element 30 for providing a signal or data to external devices. The communications signal or data can be in analog and/or digital form and can be communicated electrically, optically, and/or wirelessly, or by some combination of the foregoing. For example, in one embodiment, the sensor 24 can both receive power and send a communications signal by way of the communication element 30, which is shown (e.g., in FIG. 3B) to comprise a multi-pin electrical connector. In another embodiment, a sensor can receive power by way of a multi-pin electrical connector, but can send a communications signal wirelessly. In yet another embodiment, a sensor can send a communications signal by way of a multi-pin electrical connector, but can receive power wirelessly and/or by scavenging power wirelessly and/or from the substance flowing through the sensor. In still another embodiment, a sensor can wirelessly transmit a communications signal, and scavenge power wirelessly and/or from the substance flowing through the sensor, and therefore might not include an electrical connector. The signal or data can be sent wirelessly or over field wiring to a signal converter, a visual display, data logger, computer, PLC, chart recorder, relay, valve, pump, sensor, wireless access point, internet or other computer network, industrial field bus, or any other external device capable of receiving the signal or data.

Flow-head 10, sensor 24, and component parts of each, can be constructed from any material or combination of materials that is/are chemically and physically compatible with the substance to be tested and the testing environment. This can include a nearly limitless combination of metals, ceramics, plastics and other materials. Likewise, it is contemplated that these components can be manufactured using any combination of manufacturing techniques including, but not limited to, machining, casting, injection molding, material deposition, forming, or wire, laser, plasma, or water cutting. One or both of the flow-head 10 and the sensor 24 can be provided with fins or heatsinks to facilitate self-cooling for prevention of overheating. For example, the sensor 24 is shown in FIG. 1 to include fins 99. Additional or alternative cooling provisions can be provided for one or both of a flow-head and a sensor of a flow-through sensing apparatus including, for example, Peltier type cooling elements and/or provisions to facilitate closed loop or open loop cooling by fluids such as water or air. One or both of a flow-head and a sensor of a flow-through sensing apparatus can additionally or alternatively comprise resistive or inductive type heating elements.

Turning now to FIG. 4, the flow-through sensing apparatus depicted in FIG. 1 is shown in cross-section. The sensing chamber 54 is shown to be created by the fluid-tight mating of flow-head 10, chamber seal 42, and sensor 24. In operation, a substance conducted through supply conduit 20 can enter flow-head 10 through input port 12 and can be internally conducted to the sensing chamber 54 through input channel 50 and input channel opening 44. In this configuration, input port 13 can be plugged to prevent leakage of the substance.

Figure 5A:
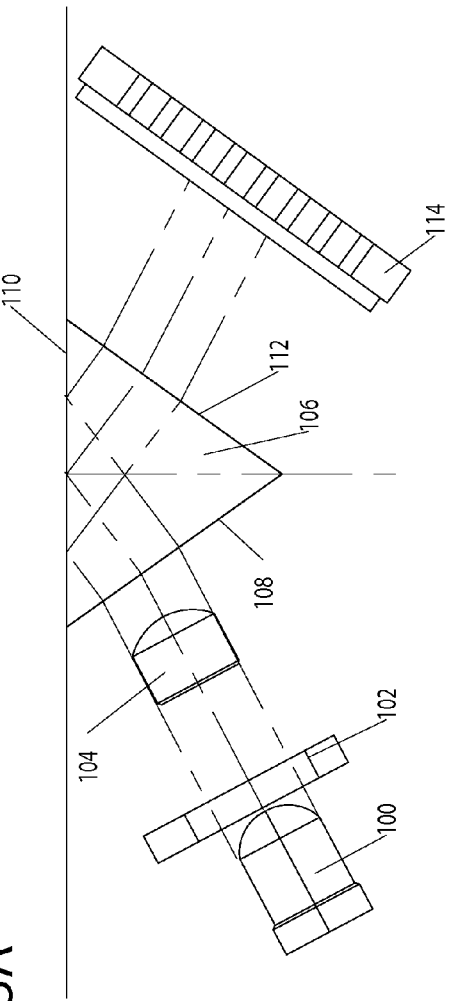
FIG. 5A is a schematic view illustrating certain components of the sensor of FIG. 3A in accordance with one embodiment.

Sensing chamber 54 can be formed in such a manner as to minimize the volume of the substance present in the sensing chamber 54, thus providing for the rapid exchange of the substance and ensuring that the substance under test is representative of the properties of the substance in a bypass and/or main process stream. Input channel opening 44 can be transversely positioned relative to sensing element 56 such as shown in FIG. 4, in such a manner as to direct the flow of the substance toward sensing element 56, which can have a cleaning effect on a sensing surface (e.g., a measuring surface 110, discussed below and shown in FIGS. 4 and 5A) of the sensing element 56. For example, with reference to FIG. 4, the flow-head 10 can be configured such that the flow of substance through the input channel 50 and from the input channel opening 44 is directed toward the sensing element 56. In one embodiment, as shown in FIG. 4, the input channel 50 can extend coaxially along a first longitudinal axis L1, the output channel 52 can extend coaxially along a second longitudinal axis L2, and each of the first and second longitudinal axes L1 and L2 can extend toward the sensing element 56. The first and second longitudinal axes L1 and L2 can converge toward one another while extending toward the sensing element 56, as shown in FIG. 4.

While in sensing chamber 54, sensing element 56 can measure physical properties of the substance and/or various process parameters. Signals from sensing element 56 can be carried to an electronic module, which in this case can be incorporated into sensing element 56, where they can be processed and then communicated to external devices through communication element 30. A pressure differential on the discharge side of flow-head 10 can cause the substance in sensing chamber 54 to be forced into the output channel opening 46, and into output channel 52, which can direct the substance to discharge conduit 22 removably connected to output port 14. In this configuration, output port 16 can be plugged to prevent leakage of the substance.

In one embodiment, sensing element 56 can include an optical sensor capable of determining the refractive index of the substance using the principle of total internal reflection. In this example, with reference to FIGS. 5A and 5B, sensing element 56 can comprise an LED 100, a light filter assembly 102, a first optical element 104, a second optical element 106, a linear array of photodiodes 114, and electronic circuitry, including temperature measuring circuitry.

LED 100, in this example, can have a peak transmission wavelength of about 589.3 nm or be so filtered as to pass only a particular wavelength of interest. Light energy emitted from LED 100 can travel along a path forming a predetermined angle of incidence relative to the measuring surface 110. This light energy can be first conditioned by light filter assembly 102, which can comprise some combination of a light filter, light diffuser, and/or polarizer, before passing through first optical element 104. First optical element 104 can be a lens positioned directly in the path of incident light energy and so constructed as to collimate or focus this light energy. Light energy transmitted by first optical element 104 can then fall on a light incident surface 108 of second optical element 106. Second optical element 106 can comprise a prism, a hemispheric element, or any of a variety of other suitable components. The second optical element 106 is shown to have the light incident face 108, the measuring surface 110 or interface which can be in physical communication with a substance of interest, and a reflected light face 112. Light energy received at the light incident face 108 can then be further directed toward measuring surface 110 of second optical element 106 at an angle relative to this surface and dependent on the refractive index of second optical element 106.

In the presence of air at the interface with measuring surface 110, all light energy can be totally internally reflected at measuring surface 110 at an angle equal to its angle of incidence. This light energy can then be directed toward and pass through reflected light face 112 of second optical element 106, and fall upon linear array 114, so positioned as to absorb all incident light energy. In this state, associated electronics scanning linear array 114 can determine that all of the photodiodes in a particular range of interest have a strong degree of light energy incident upon them.

Figure 5B:
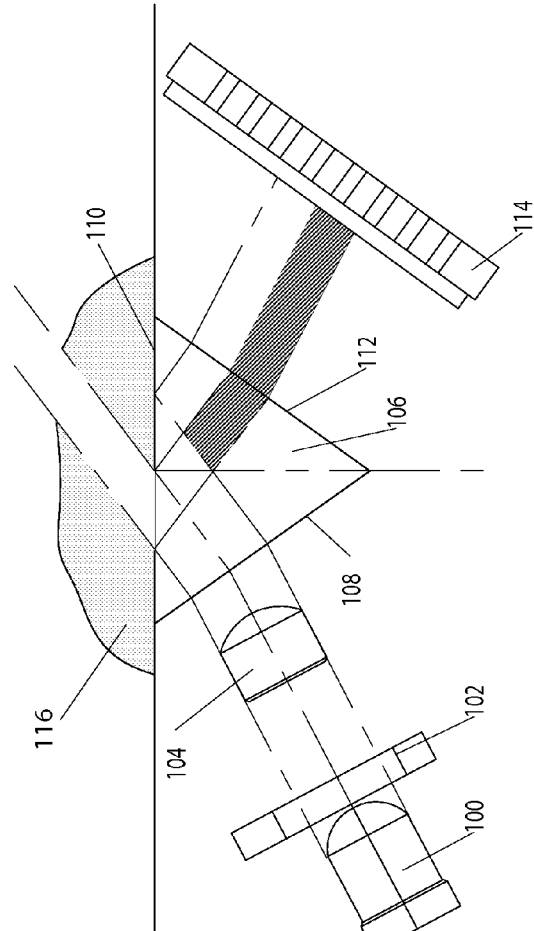
FIG. 5B is another schematic view illustrating operation of the optical sensor of FIG. 5A.

With reference to FIG. 5B, in the presence of a different substance 116 at the interface with measuring surface 110, a substance with a refractive index higher than that of ambient air, some of the light energy incident upon the measuring surface 110 can be transmitted into substance 116 and some light energy can then be directed towards and pass through reflected light face 112 of second optical element 106, and thereafter fall upon linear array 114. In this case, since some light energy was transmitted into substance 116 and lost, and still other light energy was able to be reflected onto linear array 114, the region of linear array 114 previously defined by the range of totally internally reflected light now has an illuminated region and a dark region. The boundary between this illuminated and dark region is a phenomena caused by the critical angle of the substance, relative to its refractive index, and will move up and down the face of linear array 114 depending upon changes in the refractive index or temperature of the substance. Temperature measurement circuitry within the sensing element 56 can adequately compensate for changes in the refractive index of a substance under test. After calibration of the system using solutions of known refractive index, the position of the illuminated/dark boundary on linear array 114 can be truly indicative of the refractive index of the substance being tested.

In addition or alternative to being configured for determining the refractive index of a substance, it will be appreciated that the sensing element 56 can determine temperature, pressure, ph, flow rate, and/or any of a variety of other substance and/or process parameters. In other embodiments, respective sensors 24 can be configured to measure different parameters (and/or different ranges of parameters) and can be selectively and alternatively coupled with the flow-head 10 depending upon the nature of the substance or process to be monitored, or which data is desired. In this manner, one of the sensors 24 can be quickly and simply replaced with another one of the sensors 24, and without need for tools or adjustment of conduits or other plumbing.

In one embodiment, a valve assembly (not shown) can be provided for selectively stopping the flow of a substance provided by a supply conduit and/or discharged through a discharge conduit, whether the flow-through sensing apparatus is positioned in a main process stream or in a bypass stream running parallel to the main process stream. In this configuration, in the event the flow-though sensing apparatus is positioned in a bypass stream parallel to a main process stream, flow to the apparatus can be stopped without requiring interruption of flow in the main process stream. This can eliminate the need to drain large diameter pipes that would otherwise need to be drained to facilitate removal of sensor 24.

For example, such a valve assembly can in one embodiment exist as one or more separate components located external to the flow-through sensing apparatus and can include, for example, off-the-shelf valves. However, in another embodiment, a flow-head can have one or more internal components configured to selectively stop the flow of a substance, either in response to manual force applied by an operator to a control device or in an automated manner in the event an associated sensor is decoupled from the flow-head. In the latter case, the internal component can be automatically activated during the removal of the sensor through use of mechanical or electrical components.

The sensor element 46 can require periodic cleaning depending upon the properties of the substance being measured. This cleaning may need to be performed as frequently as after each batch run, or in some cases, a process might be periodically paused to enable cleaning of the sensor 24. For this and other embodiments, one or more of the input ports (e.g., 13) can be used to selectively connect flow-head 10 of the flow-through sensing apparatus to a source of steam, hot-water, chemical agent, or other cleaning agent capable of cleaning the sensing element 56. In another embodiment, a substance with known physical properties can be automatically or manually conducted into sensing chamber 54 through an input port and brought into communication with the sensing element 56. Sensor 24 can use the measured value of the substance to automatically set its own calibration. Once the calibration operation is completed, the substance can flow through an output port into a discharge conduit or drain. It will be appreciated that valving can be provided either external or internal to the flow-head 10 to facilitate selective provision of cleaning and/or calibration agents to the sensing element 56, and/or to selectively block the passage of process substance through the flow-head 10 during the cleaning and/or calibration processes.

In this and other embodiments, power to operate the electronics housed in the sensor 24 can be sourced externally or can be generated, harvested, or scavenged from within the flow-head 10 or sensor 24 from the flow of the substance, light energy, thermal energy, thermal gradients, kinetic energy, ambient RF energy, and the like.

Figure 6:
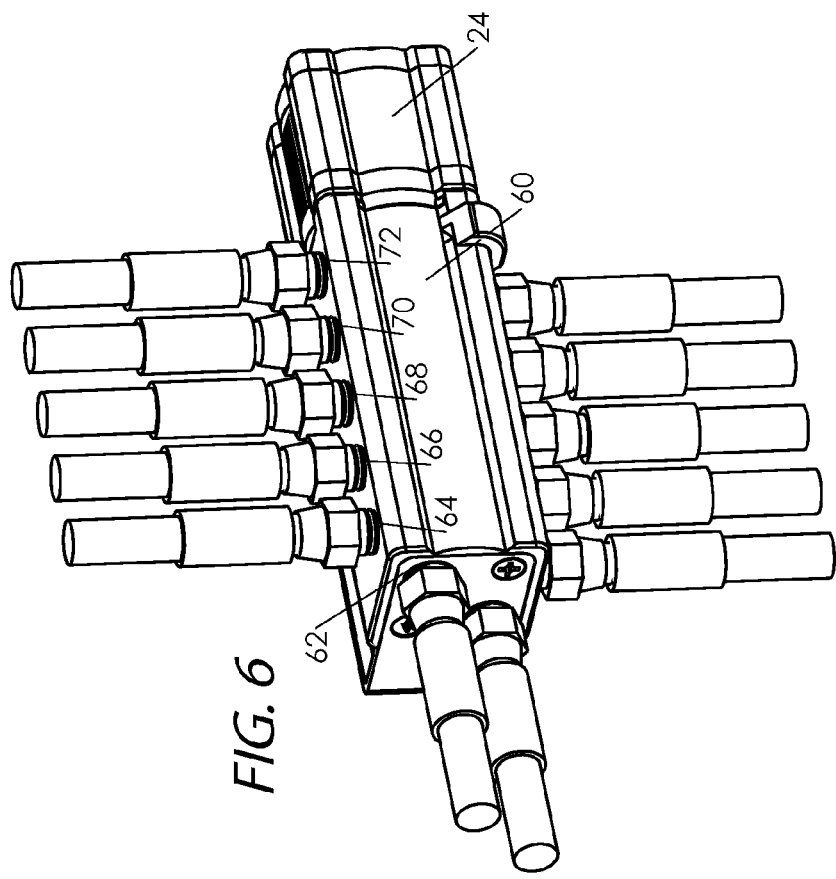
FIG. 6 is a perspective view depicting a flow-through sensing apparatus in accordance with another embodiment, wherein the flow-through sensing apparatus is in association with multiple supply conduits and at least one discharge conduit.

FIG. 6 illustrates yet another embodiment of the flow-through sensing apparatus, where flow-head 60 can act as a manifold with any number of input ports (e.g., 62, 64, 66, 68, 70 and 72) removably connected to a plurality of supply conduits for switchably supplying sensor 24 with substances from different sources. Flow-head 60 can also have any number of output ports (which may or may not be associated with input ports 62, 64, 66, 68, 70 and 72). In this embodiment, sensor 24 can do the work of many sensors.

Figure 7:
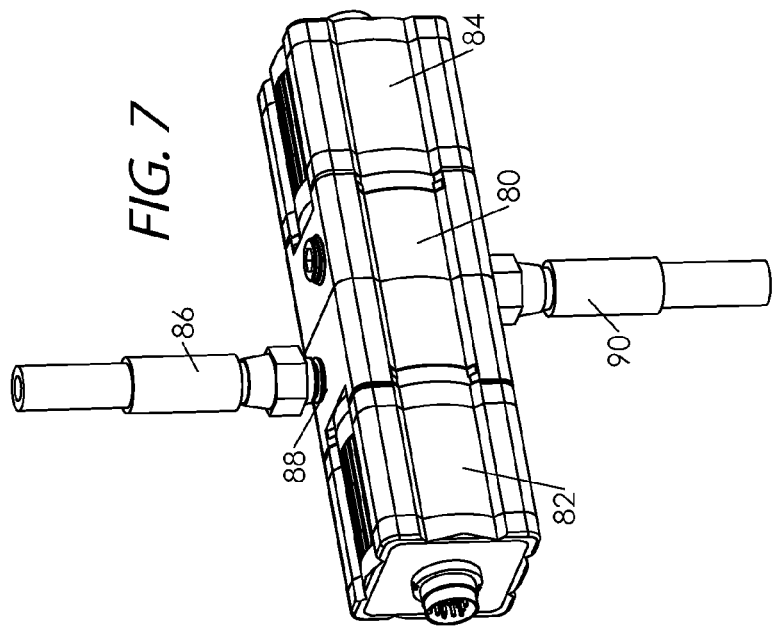
FIG. 7 is a perspective view depicting a flow-through sensing apparatus in accordance with yet another embodiment, wherein the flow-through sensing apparatus is in association with a portion of a supply conduit and a portion of a discharge conduit.

FIG. 7 illustrates yet another embodiment of the flow-through sensing apparatus, where flow-head 80 can accept one or more sensors 82 and 84. In this embodiment, a substance supplied by supply conduit 86 to input port 88 can be internally directed into respective sensing chambers corresponding with the respective sensors 82 and 84, where it physically communicates with respective sensing elements of the respective sensors 82 and 84, and is then discharged through discharge conduit 90.

An example of a method for installing a flow-through sensing apparatus will now be described. A supply conduit 20 can be attached to the input port 12 of the flow-head 10, and a discharge conduit 22 can be attached to the output port 14 of the flow-head 10. In one embodiment, the supply conduit 20 and the discharge conduit 22 cooperate with the flow-through sensing apparatus to facilitate a bypass stream that runs in parallel to a main process stream. Alternatively, the supply conduit 20 and the discharge conduit 22 cooperate with the flow-through sensing apparatus to facilitate a main process stream. In one embodiment, such as with reference to FIG. 6, a flow-head can serve as a manifold by attaching multiple supply conduits to one or more input ports of the flow-head, or by attaching multiple discharge conduits to one or more output ports of the flow-head.

The sensor 24 can be coupled with the flow head 10, through use of a quick-disconnect mechanical coupling such as a twist-lock type arrangement, to at least partially define the sensing chamber 54. Following connection of the sensor 24 to the flow-head 10, one or more valves (e.g., provided in the supply conduit and/or discharge conduit, and/or integrally to the flow-head) can be opened to facilitate flow of substance through each of the supply conduit 20 and the discharge conduit 22 relative to the sensor 24. In such a configuration, prior to disconnecting the sensor 24 from the flow-head 10, the valve(s) can be closed to prevent flow of substance through each of the supply conduit 20 and the discharge conduit 22 relative to the sensor 24. From time to time, a cleaning agent or a calibrating agent can be provided to the input port 12 of the flow-head 10 (via supply conduit 20) to facilitate cleaning or calibration of the sensor element 46, respectively. During normal operation of the flow-through sensing apparatus, the sensing element 56 can determine the refractive index, temperature, and/or other process parameter of or relating to a substance in the sensing chamber 54 and, in response, can communicate a signal for transmission to a device external to the flow-through sensing apparatus.

It will be appreciated that the flow-through sensing apparatuses of FIGS. 8 and 9A-9D can be configured and function similarly to that described above with respect to the flow-through sensing apparatus of FIG. 1, except with respect to any mechanical differences as are specifically identified above and/or as are apparent from the figures themselves.

The foregoing description of embodiments and examples has been presented for purposes of illustration and description. It is not intended to be exhaustive or limiting to the forms described. Numerous modifications are possible in light of the above teachings. Some of those modifications have been discussed and others will be understood by those skilled in the art.

The embodiments were chosen and described for illustration of various embodiments. The scope is, of course, not limited to the examples or embodiments set forth herein, but can be employed in any number of applications and equivalent devices by those of ordinary skill in the art. Rather it is hereby intended the scope be defined by the claims appended hereto.

What is claimed is:

1. A flow-through sensing apparatus, comprising:
a flow-head defining an input port and an output port and comprising a first mating feature; and
a sensor comprising a sensing element and a second mating feature; wherein:
the first mating feature is configured to selectively engage the second mating feature in a twist-lock configuration to provide a quick-disconnect mechanical coupling between the sensor and the flow-head;
when the sensor is coupled with the flow-head, the sensor cooperates with the flow-head to at least partially define a sensing chamber;
the sensing chamber is in fluid communication with each of the input port, the output port, and the sensing element; and
the sensing element is configured to determine the refractive index of a substance in the sensing chamber.

2. The flow-through sensing apparatus of claim 1 being configured such that a partial-turn of the sensor relative to the flow-head results in movement of the sensor relative to the flow-head between an unlocked position and a fully locked position.

3. The flow-through sensing apparatus of claim 2 wherein the partial-turn comprises an eighth-turn.

4. The flow-through sensing apparatus of claim 2 further comprising a retractable locking mechanism configured for preventing inadvertent rotation of the sensor relative to the flow-head.

5. The flow-through sensing apparatus of claim 4 wherein:
the flow-head comprises the retractable locking mechanism;
the retractable locking mechanism comprises a thumb-lever, a pin, and a spring; and
the thumb-lever is configured for sliding the pin against a bias of the spring.

6. The flow-through sensing apparatus of claim 1 wherein the flow-head further defines an input channel and an output channel, the input channel has an input channel opening, the output channel has an output channel opening, the input port is in fluid communication with each of the input channel and the input channel opening, the output port is in fluid communication with each of the output channel and the output channel opening, and the input channel opening is transversely positioned relative to the sensing element to direct the flow of a substance toward the sensing element.

7. The flow-through sensing apparatus of claim 6 wherein: the input channel extends coaxially along a first longitudinal axis; the output channel extends coaxially along a second longitudinal axis; and each of the first longitudinal axis and the second longitudinal axis extends toward the sensing element.

8. The flow-through sensing apparatus of claim 7 wherein the first longitudinal axis and the second longitudinal axis converge toward one another while extending toward the sensing element.

9. The flow-through sensing apparatus of claim 1 wherein:
the flow-head comprises a first body;
the first mating feature comprises a first flange extending from the first body;
the sensor comprises a second body; and
the second mating feature comprises a second flange extending from the second body.

10. The flow-through sensing apparatus of claim 1 wherein:
the first flange cooperates with the first body to define a groove; and
when the sensor is coupled with the flow-head, the second flange is received within the groove and is sandwiched between the first flange and the first body.

11. The flow-through sensing apparatus of claim 1 further comprising a chamber seal provided on one of the sensor and the flow-head and configured to facilitate a seal between the sensor and the flow-head when the sensor is coupled with the flow-head.

12. The flow-through sensing apparatus of claim 11 wherein:
the flow-head defines an annular channel;
the chamber seal comprises an O-ring; and
the O-ring is at least partially received within the annular channel.

13. The flow-through sensing apparatus of claim 1 wherein the sensing element is further configured to determine a temperature of a substance in the sensing chamber.

14. The flow-through sensing apparatus of claim 1 wherein the sensing element comprises an optical sensor capable of determining the refractive index of a substance in the sensing chamber through use of the principle of total internal reflection.

15. The flow-through sensing apparatus of claim 1 wherein the sensor further comprises electronic circuitry configured for converting signals from the sensing element into usable data or signals for communication to a device external to the sensor.

16. The flow-through sensing apparatus of claim 1 wherein:
the input port comprises at least two respective threaded apertures in the flow-head in fluid communication with one another; and
the output port comprises at least two respective threaded apertures in the flow-head in fluid communication with one another.

17. A flow-through sensing apparatus, comprising: a flow-head defining an input port and an output port; and a sensor comprising a sensing element; wherein the flow-head and the sensor cooperate to define means for quick-disconnect mechanically coupling the sensor and the flow-head;
wherein, when the sensor is coupled with the flow-head, the sensor cooperates with the flow-head to at least partially define a sensing chamber, with the sensing chamber being in fluid communication with each of the input port, the output port, and the sensing element;
wherein the sensing element comprises means for determining the refractive index of a substance in the sensing chamber.

18. The flow-through sensing apparatus of claim 17 wherein the flow-head comprises means for directing the flow of a substance toward the sensing element.

19. The flow-through sensing apparatus of claim 17 further comprising means for facilitating a seal between the sensor and the flow-head when the sensor is coupled with the flow-head.

20. The flow-through sensing apparatus of claim 17 wherein the sensor further comprises means for converting signals from the sensing element into usable data or signals for communication to a device external to the sensor.

21. A sensor configured for quick-disconnect mechanical coupling with a flow-head, the sensor comprising:
a sensing element; and
a mating feature configured to selectively engage a flow-head in a twist-lock configuration to provide a quick-disconnect mechanical coupling between the sensor and a flow-head;
wherein, when the sensor is coupled with a flow-head, the sensor cooperates to at least partially define a sensing chamber, with the sensing chamber being in fluid communication with the sensing element, and the sensing element configured to determine the refractive index of substance in the sensing chamber.

22. The sensor of claim 21 wherein the sensor comprises fins configured to facilitate self-cooling of the sensor.

23. The sensor of claim 21 wherein the sensor further comprises electronic circuitry configured for converting signals from the sensing element into usable data or signals for communication to a device external to the sensor.

24. The sensor of claim 21 wherein the sensing element is further configured to determine a temperature of a substance in the sensing chamber.

* * * * *